(12) United States Patent
Cao et al.

(10) Patent No.: US 11,191,950 B2
(45) Date of Patent: Dec. 7, 2021

(54) HIGH RESOLUTION BRAIN-ELECTRONICS INTERFACE

(71) Applicant: INTERNATIONAL BUSINESS MACHINES CORPORATION, Armonk, NY (US)

(72) Inventors: Qing Cao, Yorktown Heights, NY (US); Hariklia Deligianni, Alpine, NJ (US); Fei Liu, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 158 days.

(21) Appl. No.: 16/542,574

(22) Filed: Aug. 16, 2019

(65) Prior Publication Data

US 2019/0366073 A1 Dec. 5, 2019

Related U.S. Application Data

(62) Division of application No. 15/466,171, filed on Mar. 22, 2017, now Pat. No. 10,576,268.

(51) Int. Cl.
*A61N 1/05* (2006.01)
*H01L 21/762* (2006.01)
(Continued)

(52) U.S. Cl.
CPC .............. *A61N 1/0529* (2013.01); *A61B 5/24* (2021.01); *A61B 5/291* (2021.01); *A61B 5/4094* (2013.01); *A61B 5/6868* (2013.01); *A61N 1/0531* (2013.01); *A61N 1/36064* (2013.01); *A61N 1/36067* (2013.01); *H01L 21/76251* (2013.01); *A61B 2562/125* (2013.01);
(Continued)

(58) Field of Classification Search
CPC ................ A61N 1/0529; A61N 1/0531; A61N 1/36064; A61N 1/36067; A61B 5/24; A61B 5/291; A61B 5/6868; A61B 5/4094; A61B 2562/164; A61B 2562/125; H01L 21/76251; H01L 21/304; H01L 21/7806
See application file for complete search history.

(56) References Cited

U.S. PATENT DOCUMENTS 3,826,244 A * 7/1974 Salcman ................. A61L 31/10
 600/377
5,692,516 A * 12/1997 Kaneko ................... A61B 5/283
 600/544

(Continued)

OTHER PUBLICATIONS

List of IBM Patents or Patent Applications Treated as Related; (Appendix P), Date Filed Aug. 16, 2019; 2 pages.

(Continued)

*Primary Examiner* — Mark W. Bockelman
(74) *Attorney, Agent, or Firm* — Cantor Colburn LLP; Robert Sullivan

(57) ABSTRACT

Aspects include high resolution brain-electronic interfaces and related methods. Aspects include forming a semiconductor circuit on a substrate, depositing a tensile stress layer on the circuit, and separating the semiconductor circuit from a portion of the silicon substrate. Aspects also include removing the tensile stress layer from the semiconductor circuit and transferring the semiconductor circuit to a biocompatible film.

5 Claims, 13 Drawing Sheets

(51) Int. Cl.
*A61B 5/00* (2006.01)
*A61N 1/36* (2006.01)
*A61B 5/04* (2006.01)
*A61B 5/24* (2021.01)
*A61B 5/291* (2021.01)
*H01L 21/304* (2006.01)
*H01L 21/78* (2006.01)

(52) U.S. Cl.
CPC ....... *A61B 2562/164* (2013.01); *H01L 21/304* (2013.01); *H01L 21/7806* (2013.01)

(56) References Cited

U.S. PATENT DOCUMENTS

| | | | |
|---|---|---|---|
| 7,751,877 B2 * | 7/2010 | Flaherty | A61B 5/0031 600/544 |
| 7,905,013 B2 | 3/2011 | Zhang et al. | |
| 8,039,847 B2 | 10/2011 | Nuzzo et al. | |
| 8,666,471 B2 | 3/2014 | Rogers et al. | |
| 8,886,334 B2 | 11/2014 | Ghaffari et al. | |
| 8,934,965 B2 | 1/2015 | Rogers et al. | |
| 9,008,780 B2 | 4/2015 | Nudo et al. | |
| 9,434,150 B2 | 9/2016 | Bower et al. | |
| 9,450,043 B2 | 9/2016 | Nuzzo et al. | |
| 2006/0161218 A1 | 7/2006 | Danilov | |
| 2007/0037323 A1 | 2/2007 | Henley | |
| 2015/0237711 A1 | 8/2015 | Rogers et al. | |
| 2015/0305643 A1 | 10/2015 | Negi et al. | |
| 2018/0272123 A1 | 9/2018 | Cao et al. | |

OTHER PUBLICATIONS

Hwang, S. W., Kim, D. H., Tao, H., et al. (2013). Materials and Fabrication Processes for Transient and Bioresorbable High-Performance Electronics. Advanced Functional Materials, 23(33), 4087-4093.

Lee, J. H., Kim, H., Kim, J. H., et al. (2016). Soft implantable microelectrodes for future medicine: prosthetics, neural signal recording and neuromodulation. Lab on a Chip, 16(6), 959-976.

Pashale, R., Anikeeva, P., Lee, J. H., et al. (2014). Optogenetic brain interfaces. IEEE reviews in biomedical engineering, 7, 3-30.

* cited by examiner

HIGH RESOLUTION BRAIN-ELECTRONICS INTERFACE

DOMESTIC PRIORITY

This application is a divisional of U.S. application Ser. No. 15/466,171, titled "High Resolution Brain-Electronics Interface" filed Mar. 22, 2017, the contents of which are incorporated by reference herein in its entirety.

BACKGROUND

The present invention relates in general to brain-electronic interfaces, and more specifically, to high resolution brain-electronic interfaces including active electronics.

A brain-computer interface (BCI), which can also be referred to as a brain-electronic interface, direct neural interface (DNI), synthetic telepathy interface (STI) or brain-machine interface (BMI), can provide a direct communication pathway between the brain and an external electronic device. BCIs can provide direct electronic communication to neuronal cells in the brain, providing numerous potential therapeutic and investigational benefits. For example, BCIs can be directed at assisting, augmenting, or repairing human cognitive or sensory-motor functions. BCIs are under investigation for assistance with the use and direction of prosthetic limbs, for use and enhancement of hearing aids, and for investigations associated with neurodegenerative disorders.

SUMMARY

Embodiments of the invention are directed to a method of fabricating a high-resolution brain-electronic interface. A non-limiting example of the method includes forming a semiconductor circuit on a silicon substrate, wherein the semiconductor circuit includes a plurality of components. A tensile stress layer is deposited on the semiconductor circuit to cause a fracture in the silicon substrate. The semiconductor circuit is separated from a portion of the silicon substrate at the fracture in the substrate to generate a semiconductor circuit layer on a thinned silicon layer. The tensile stress layer is removed from the semiconductor circuit. The semiconductor circuit is transferred to a biocompatible/bio-absorbable film.

Embodiments of the invention are directed to a high resolution brain-electronic interface. An exemplary high resolution brain-electronic interface includes a semiconductor circuit including a plurality of components. The high resolution brain-electronic interface also includes a silk film. At least some of the plurality of components are spaced apart less than or equal to 10 micrometers Embodiments of the invention are directed to a method of treating a neurodegenerative disease. A non-limiting example of the method includes opening a skull to expose a brain surface. A semiconductor circuit comprising a plurality of components and a biocompatible film can be applied to the brain surface. A voltage change of a single neuron on the brain surface with one of the plurality of components can be detected.

BRIEF DESCRIPTION OF THE DRAWINGS

The foregoing and other features and advantages of the one or more embodiments described herein are apparent from the following detailed description taken in conjunction with the accompanying drawings in which:

FIGS. 1A-1H illustrate an exemplary fabrication process for forming a high resolution brain-electronic interface according to one or more embodiments of the present invention, in which:

FIG. 1A is a cross-sectional side view of a semiconductor structure after formation of an oxide layer on a silicon substrate;

FIG. 1B is a cross-sectional side view of a semiconductor structure after formation of a semiconductor circuit layer;

FIG. 1C is a cross-sectional side view of a semiconductor structure after deposition of a metal stress layer and a thermal release tape;

FIG. 1D is a cross-sectional side view of a semiconductor structure demonstrating spalling a thin silicon layer from the silicon substrate;

FIG. 1E is a cross-sectional side view of a semiconductor structure after removing the thin silicon layer and transferring the structure to a sacrificial polymer;

FIG. 1F is a cross-sectional side view of a semiconductor structure after removing the thermal release tape and metal stress layer;

FIG. 1G is a cross-sectional side view of a semiconductor structure after forming a biocompatible film on the semiconductor circuit layer; and FIG. 1H is a cross-sectional side view of a semiconductor structure after removing the sacrificial polymer and oxide layer.

FIGS. 2A-2B illustrate an exemplary fabrication process of transferring a high resolution electronic structure to a flexible substrate according to one or more embodiments, in which:

FIG. 2A is a cross-sectional view illustrating a high resolution electronic structure and a cast silk film;

FIG. 2B is a cross-sectional view of a semiconductor structure transferring the high resolution electronic structure to the cast silk film;

FIGS. 3A-3C illustrate an exemplary process of forming a brain-computer interface, in which:

FIG. 3A is a cross-sectional view of a high resolution electronic structure on a flexible film;

FIG. 3B is a cross-sectional view after depositing the high resolution electronic structure on a brain surface; and FIG. 3C is a cross-sectional view illustrating optional dissolution of the flexible film.

DETAILED DESCRIPTION

Figure 1A:
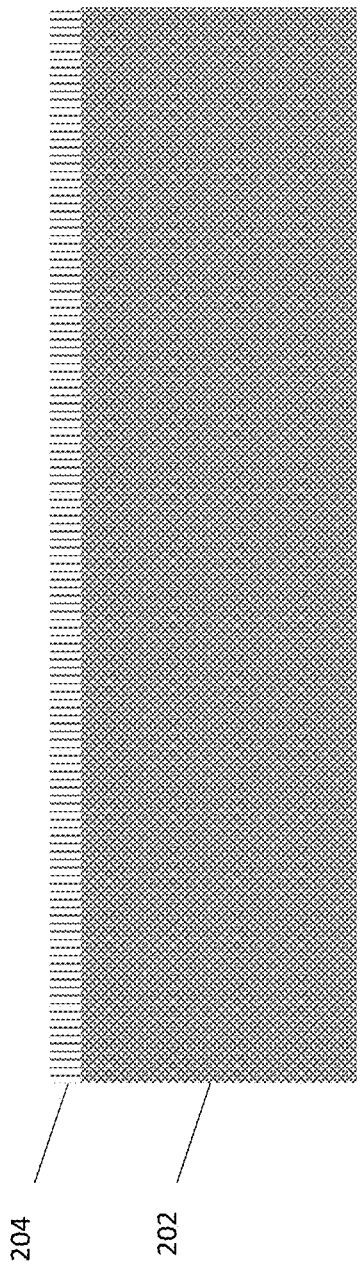

Brain-computer interfaces present therapeutic and investigational possibilities in areas of human cognitive and sensory motor functions. Some brain-computer interface systems exist in prototype form. However, performance of such brain-computer interfaces can be limited to the use of passive electronics, which have more limited functionality than active electronics. In addition, passive electrodes can require individual connections of each electrode to remote electronics. Such individual connections can impose significant spatial requirements, precluding the formation of high-resolution interfaces over relatively broad regions of the brain. For instance, spatial needs of passive electronic interfaces can preclude formation of an interface with a resolution of less than 1 millimeter over a potentially desirable area of a brain surface with dimensions of 8 cm×8 cm.

Optimal resolution for a brain-computer interface can include a resolution capable of detecting a voltage change or capable of signaling a single neuronal cell on the brain surface. Thus, because a neuronal cell can have a diameter on the order of a micrometer, a brain-computer interface with a resolution of one micrometer or lower can provide optimal functionality for use in a variety of applications. As such resolutions, detection of a signal from a single neuron can be achieved. Moreover, in some applications, stimulation of a single neuron in isolation can be achieved. Embodiments of the present invention can provide a complex high resolution circuit on a biocompatible flexible substrate, enabling transfer of the complex surface to the non-uniform and relatively delicate surface of the brain.

Embodiments of the present invention can provide high-resolution brain-computer interfaces. In some embodiments of the invention, brain-computer interfaces include complex and very large scale integrated systems. Embodiments of the invention can include brain-electronic interfaces having a resolution at or equal to the size of a single neuron, such as less than or equal to 1 micrometer. In some embodiments, the invention includes brain-electronic interfaces capable of sensing or stimulating a single neuron on a brain surface. Embodiments of the present invention include multiplexed and/or amplified sensors spaced less than 10 micrometers apart and, in some embodiments, less than 1 micrometer apart.

In some embodiments, the invention provides high-resolution brain-electronic interfaces for improved medical treatment, for instance improved treatment of diseases and conditions that benefit from neuronal stimulation or mapping. In some embodiments, high resolution brain-electronic interfaces of the invention are used for the treatment and study of neurodegenerative diseases, such as Parkinson's disease, Turret's syndrome, or epilepsy. For example, embodiments of the invention can provide improvements in the study and treatment of epilepsy through mapping the cortical area of the brain or through pinpointing the location of an epileptic seizure center. In some embodiments, for instance, embodiments of the invention are components of sensory motor systems, such as components of prosthetic limb systems.

Turning now to a more detailed description of embodiments of the present invention, FIGS. 1A-1H illustrate an exemplary fabrication process for forming a high resolution brain-electronic interface. FIG. 1A is a cross-sectional side view of a semiconductor structure after formation of an insulator layer 204 on a silicon substrate 202. Silicon substrate 202 can include, for example, silicon or a silicon compound, such as single- or poly-crystalline silicon, or silicon germanium. In some embodiments, the insulator layer 204 includes an oxide, such as silicon oxide. The insulator layer 204, for example, can be a buried oxide (BOX) layer. In some embodiments, the insulator layer 204 has a thickness of 10 to 90 nanometers (nm), such as 20 to 30 nm.

Figure 1B:
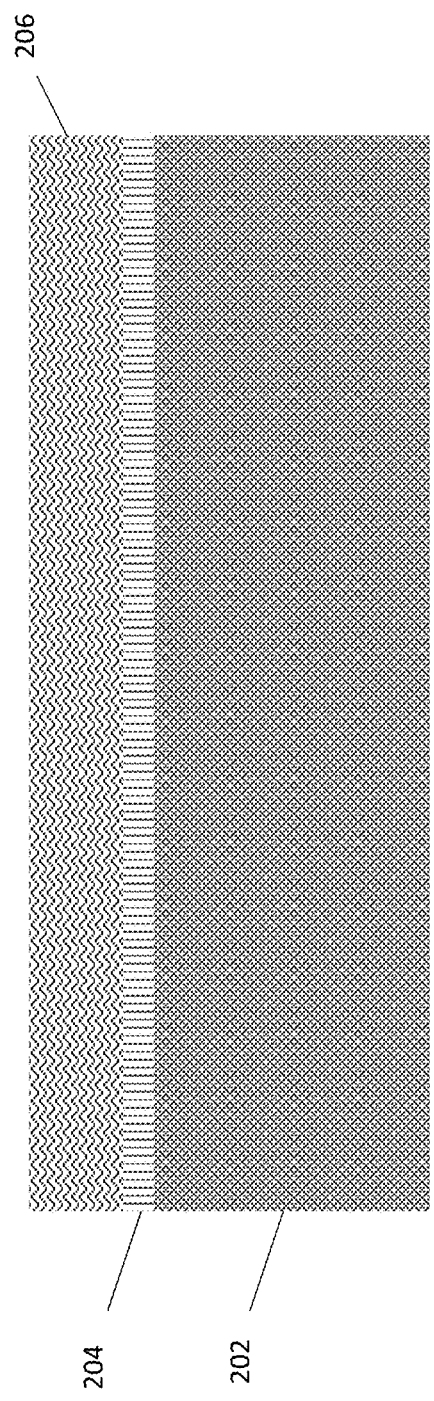

FIG. 1B is a cross-sectional side view of the semiconductor structure of FIG. 1A after formation of a semiconductor circuit layer 206. The semiconductor circuit layer 206 can include a plurality of components, including any components useful for detecting and processing neural activity. In some embodiments, the semiconductor circuit layer 206 includes active electrodes, passive electrodes, or combinations thereof. Passive electrodes can include, for example, sensors capable of detecting neuronal activity in a patient. Active electrodes can provide greater functionality in in neurological applications, for instance, by multiplexing and amplifying the electrical current. The semiconductor circuit layer 206 can be fabricated according to known microfabrication techniques.

Active electrodes can have improved density in comparison with passive electrodes and can have built in circuitry for signal processing, making them desirable for a number of applications, including the study of neural activity. For example, and not by way of limitation, semiconductor circuit layer 206 can include multiplexers (MUX) or demultiplexers (deMUX), signal conditioning circuits such as amplifiers and filters, sensors, and electrodes and can include silicon based semiconducting materials, metals, carbon nanotubes, graphene nanoribbons, or other related materials. Components of the semiconductor circuit layer 206 can be connected to one another or to external components by a plurality of circuit wires (not shown).

In some embodiments, the semiconducting circuit layer 206 includes a plurality of sensors. Sensors can include electronic components capable of receiving a signal from biological tissue, including neuronal cells and brain tissue. Exemplary signals from biological tissue can include, but are not limited to, action potential, pH, temperature, or local field potential. Sensors can also include, in some embodiments, electronic components capable of providing an output to biological tissue or to other electronic components. In some embodiments, for example, sensors can include electrodes that provide an electrical signal to adjacent biological tissue. Sensors can include, for instance, action potential sensors, pH sensors, or local field potential (LFP) sensors.

Figure 1C:
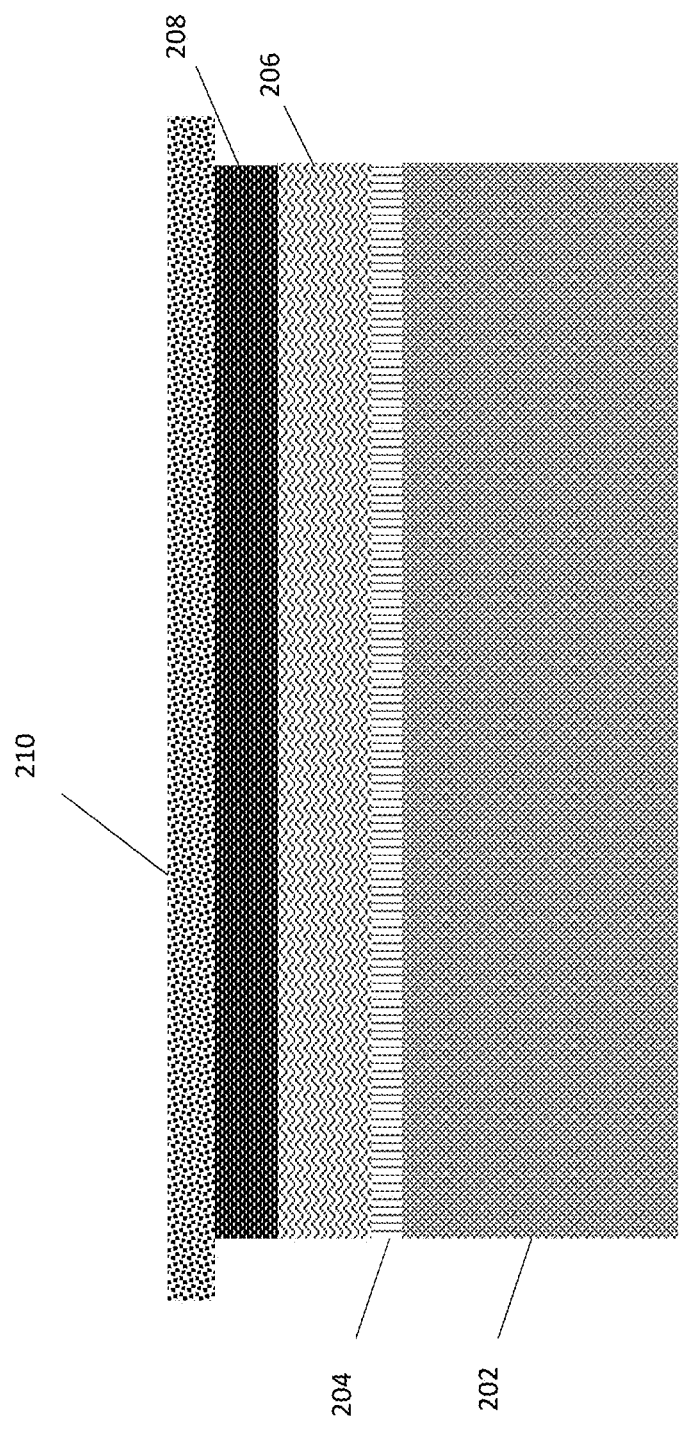

In some embodiments, an exemplary fabrication process includes depositing a tensile stress layer on the semiconductor circuit layer 206. FIG. 1C is a cross-sectional side view of a semiconductor structure after deposition of a tensile stress layer 208 on the semiconducting circuit layer 206. The tensile stress layer 208 can create mechanical stress on the structure and can include any material useful for spalling a thin silicon ribbon from a silicon substrate, such as a tensile stressed metal or metal alloy. In some embodiments, the tensile stress layer 208 includes a high stress metal, such as nickel or platinum. In some embodiments, the tensile stress layer 208 is a nickel layer. Nickel, for example, can be electrodeposited on the structure and can provide controlled stress to the structure for subsequent spalling. The tensile stress layer 208 can have a thickness, for example of 1 to 10 micrometers (μm). In some embodiments, the tensile stress layer 208 has a thickness of 1 to 2 μm. As is illustrated in FIG. 1C, a release layer 210 can be applied to the structure on top of the tensile stress layer 208. The release layer 210 can include, for instance, a plastic or metal foil that is operatively associated with, i.e., glued, adhered, or bonded to the tensile stress layer 208. In some embodiments, the release layer 210 is a thermal release tape, such as a polyimide tape.

Figure 1D:
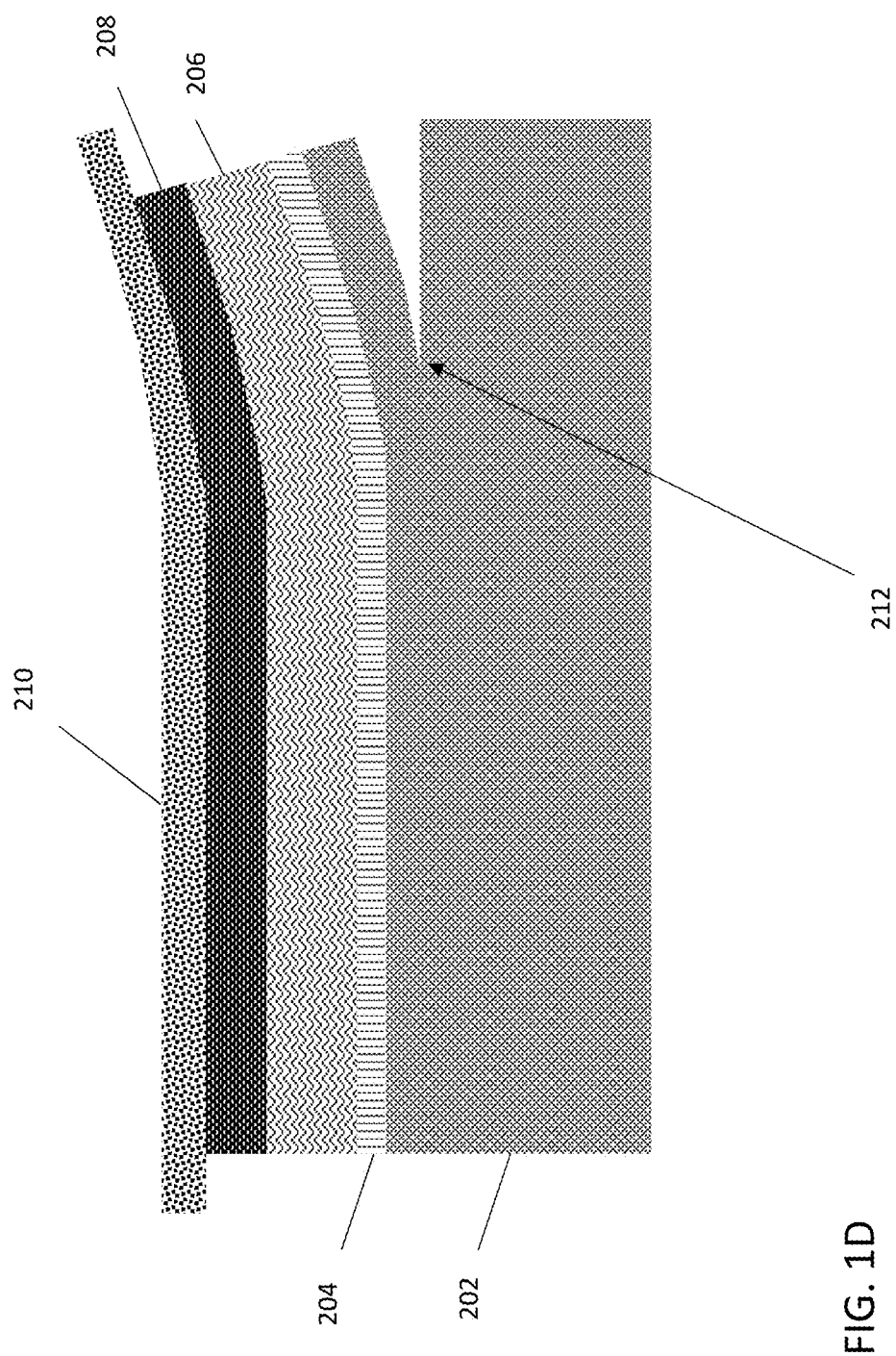

After application of the release layer 210, as is illustrated in FIG. 1D, a method of fabrication can include separating the semiconductor circuit layer 206 from a portion of the silicon substrate 202 at the fracture in the substrate 212 to generate a semiconductor circuit layer on a thinned silicon layer. In some embodiments, the thinned silicon layer is from 1 to 100 μm thick.

Figure 1E:
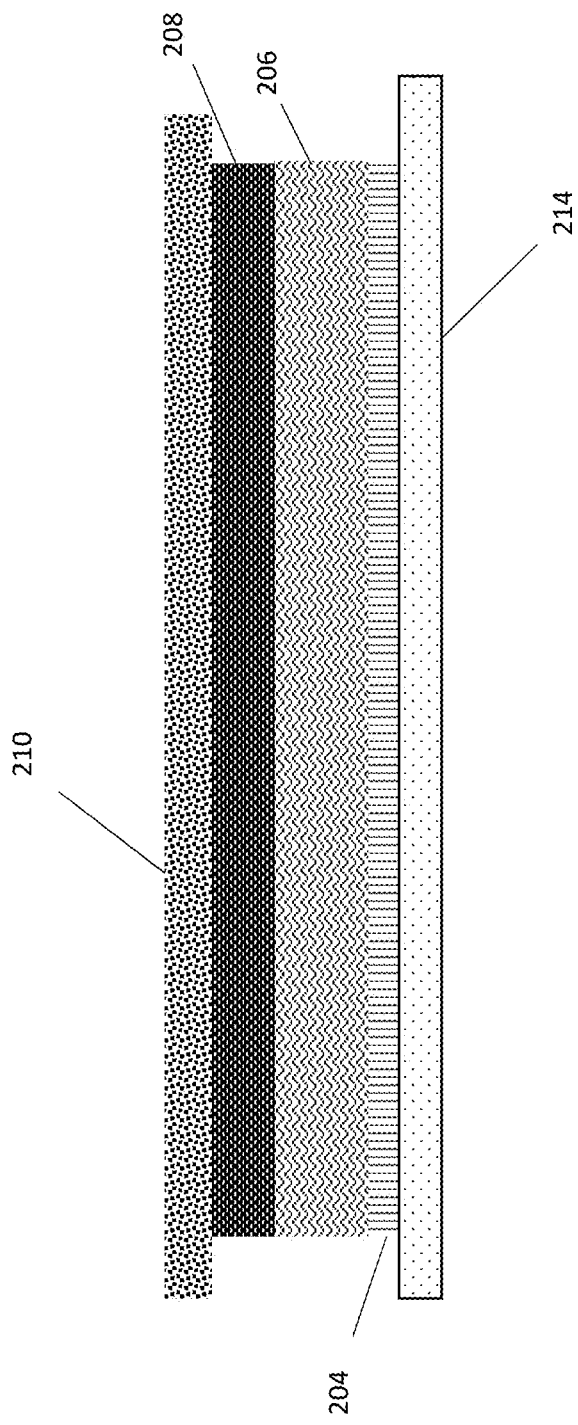

In some embodiments, a method of fabrication includes removing the thinned silicon layer. For example, the thinned silicon layer can be removed to the level of a buried oxide layer by wet etching. In some embodiments, the semiconductor circuit layer 206 can be transferred to a sacrificial polymer, such as a silicon/polymer substrate. FIG. 1E is a cross-sectional side view of a semiconductor structure after removing the thinned silicon layer and transferring the semiconductor circuit layer 206 to a sacrificial polymer 214. The sacrificial polymer 214 can be any dissolvable polymer or removable release tape that can provide mechanical support to the semiconductor circuit layer 206. In some embodiments, the sacrificial polymer 214 includes polymethylmethacrylate (PMMA) or PMMA-silica (PMMA/Si).

Figure 1F:
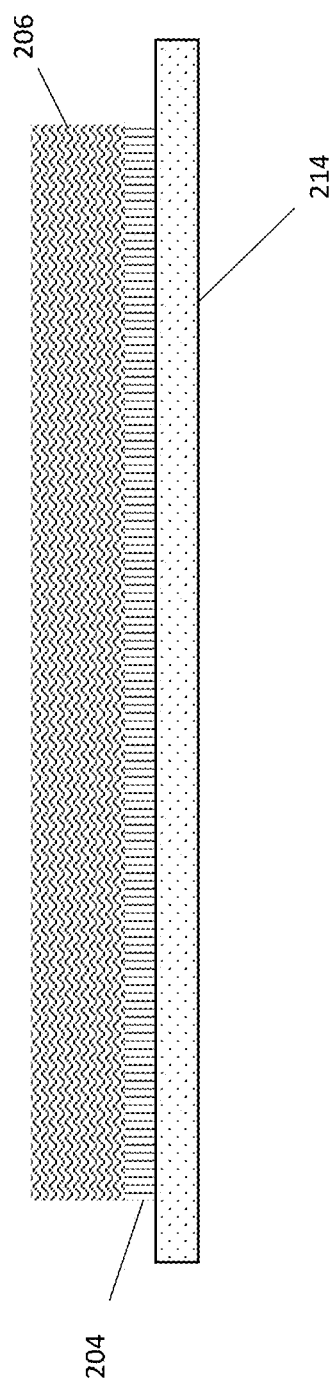

In some embodiments, after transferring the semiconductor circuit layer 206 to a sacrificial polymer 214, the release layer 210 is removed to expose the tensile stress layer 208. For example, in some embodiments the release layer 210 includes a thermal tape and is removed under thermal treatment. In some embodiments, after removing the release layer 210, a method of fabrication includes removing the tensile stress layer. For example, a nickel tensile stress layer can be removed with a wet-etch technique. FIG. 1F is a cross-sectional side view of a semiconductor structure after removing the release layer and tensile layer demonstrating a structure with an exposed semiconductor circuit layer 206 and insulating layer 204, which can be a buried oxide layer, on a sacrificial polymer 214.

Figure 1G:
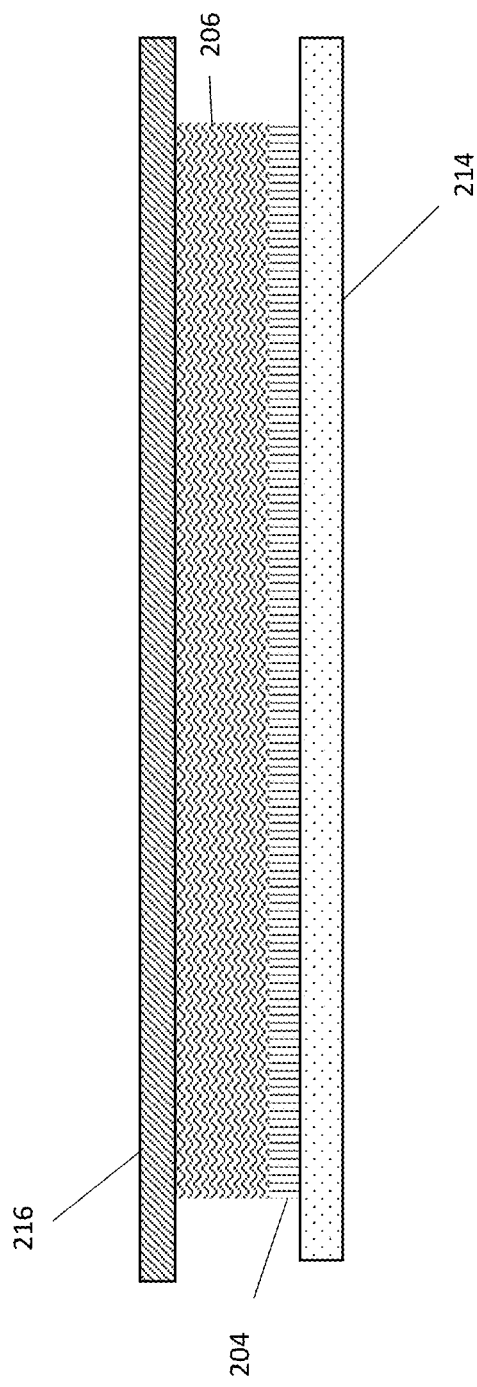

In some embodiments, as is illustrated FIG. 1G, a method of fabrication includes forming a biocompatible film 216 on the semiconductor circuit layer 206. The biocompatible film can be any flexible biocompatible substrate capable of transferring the semiconductor circuit layer 206 to a surface. In some embodiments, the biocompatible film 216 is a silk film. For example, a silk film can be formed of a silk solution by known techniques, such as casting a silk solution on a substrate. An exemplary substrate suitable for casting the biocompatible film includes polydimethylsiloxane (PDMS).

Figure 1H:
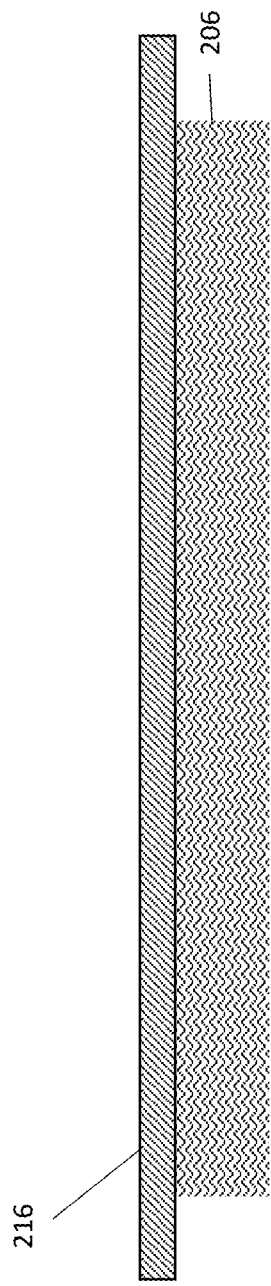

FIG. 1H is a cross-sectional side view of a semiconductor structure including a semiconductor circuit layer 206 attached to a biocompatible film 216 after removing the sacrificial polymer and oxide layer. The semiconductor circuit layer 206 can be transferred, by way of support and mechanical structure provided by the biocompatible film 216, to another surface, including a human tissue surface.

Figure 2A:
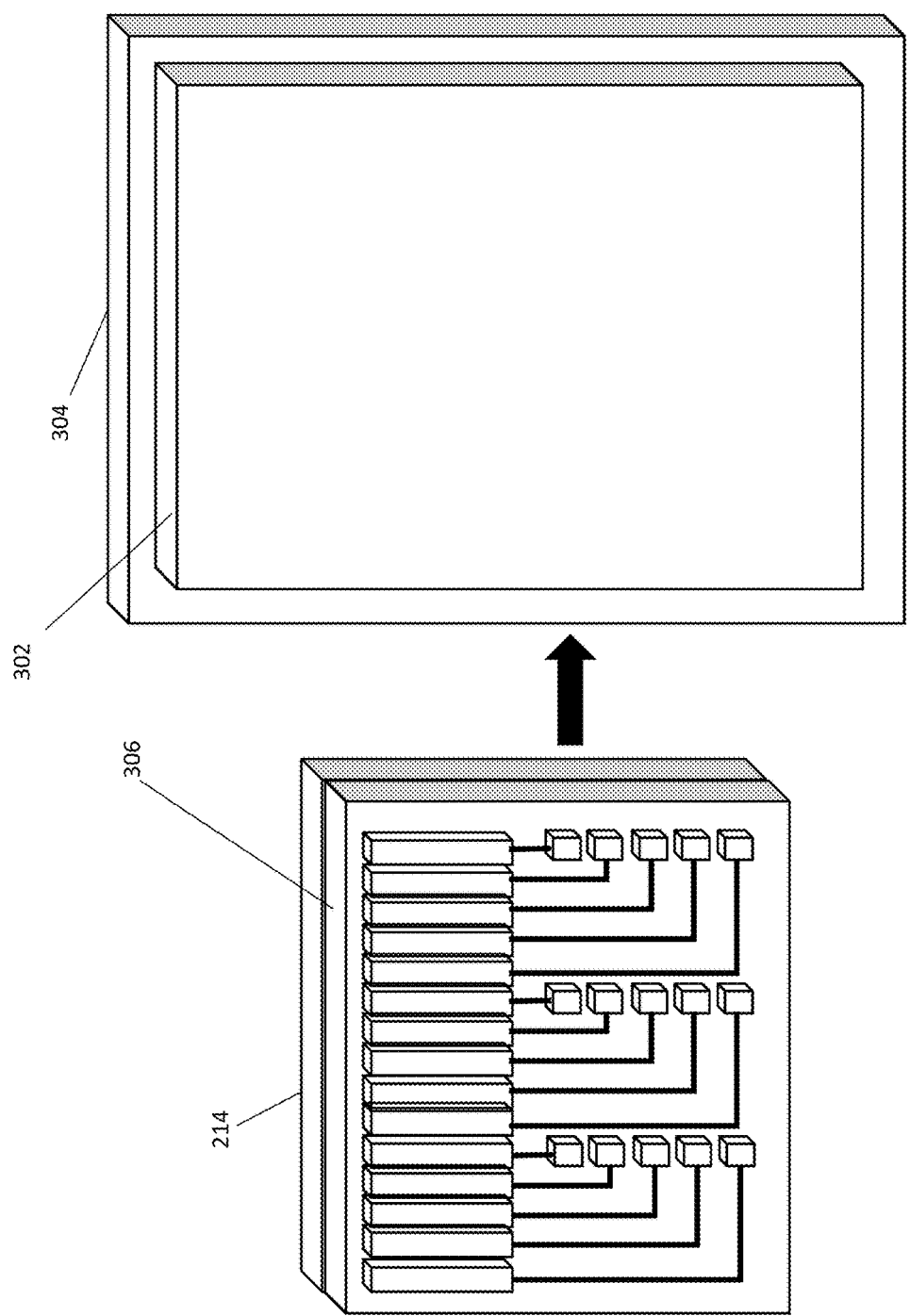
Figure 2B:
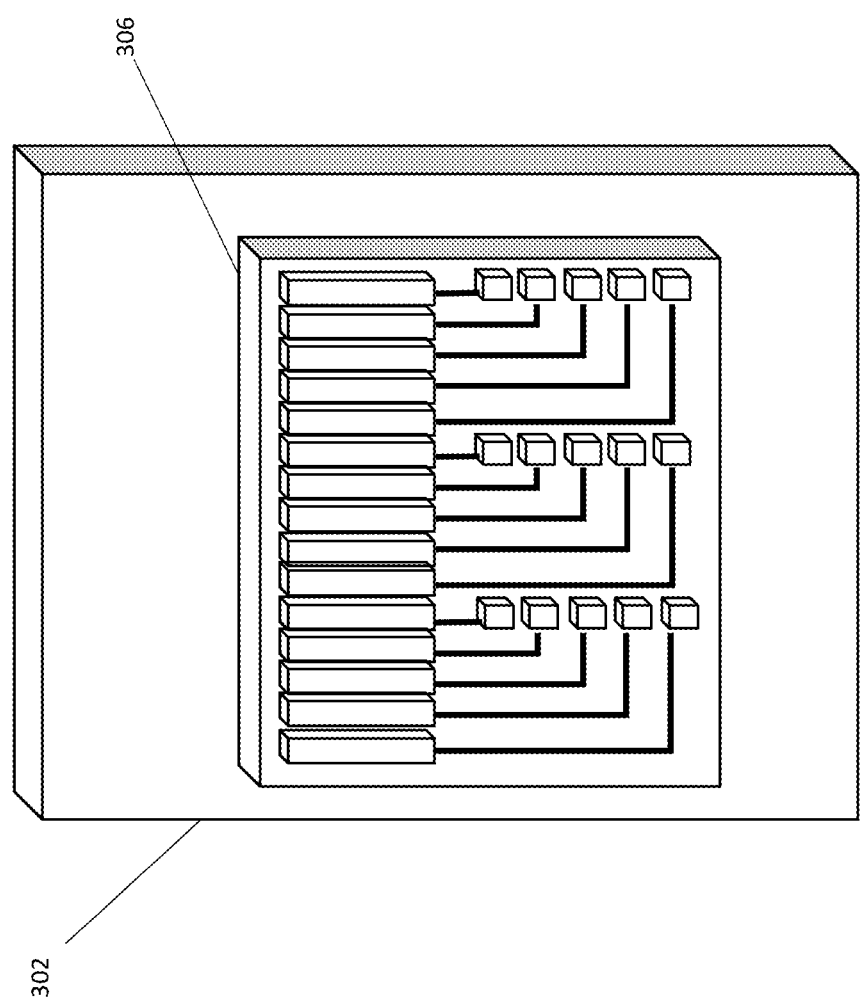

FIGS. 2A-2B illustrate an exemplary fabrication process of transferring a high resolution electronic structure to a flexible substrate. FIG. 2A is a cross-sectional view illustrating a high resolution electronic structure 306, which can include a semiconductor circuit layer, on a sacrificial polymer 214 and a silk film 302 cast on a PDMS substrate 304. The sacrificial polymer 214 can be removed, for example by dissolution and the circuit transferred to the silk film 302. In some embodiments, a silk solution precursor can be spin coated on top of the high resolution electronic structure 306 as it is supported by the sacrificial polymer 214 and, subsequently, the sacrificial polymer 214 can be removed.

FIG. 2B is a top view of a semiconductor structure transferring the high resolution electronic structure 306 to the cast silk film 302.

Figure 3A:
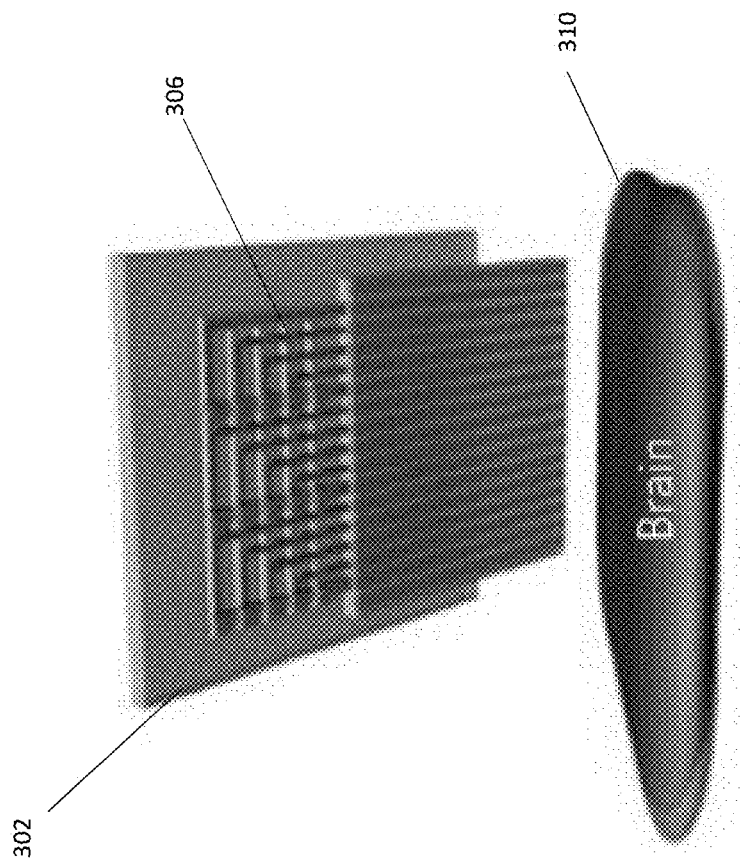
Figures 3B, 3C:
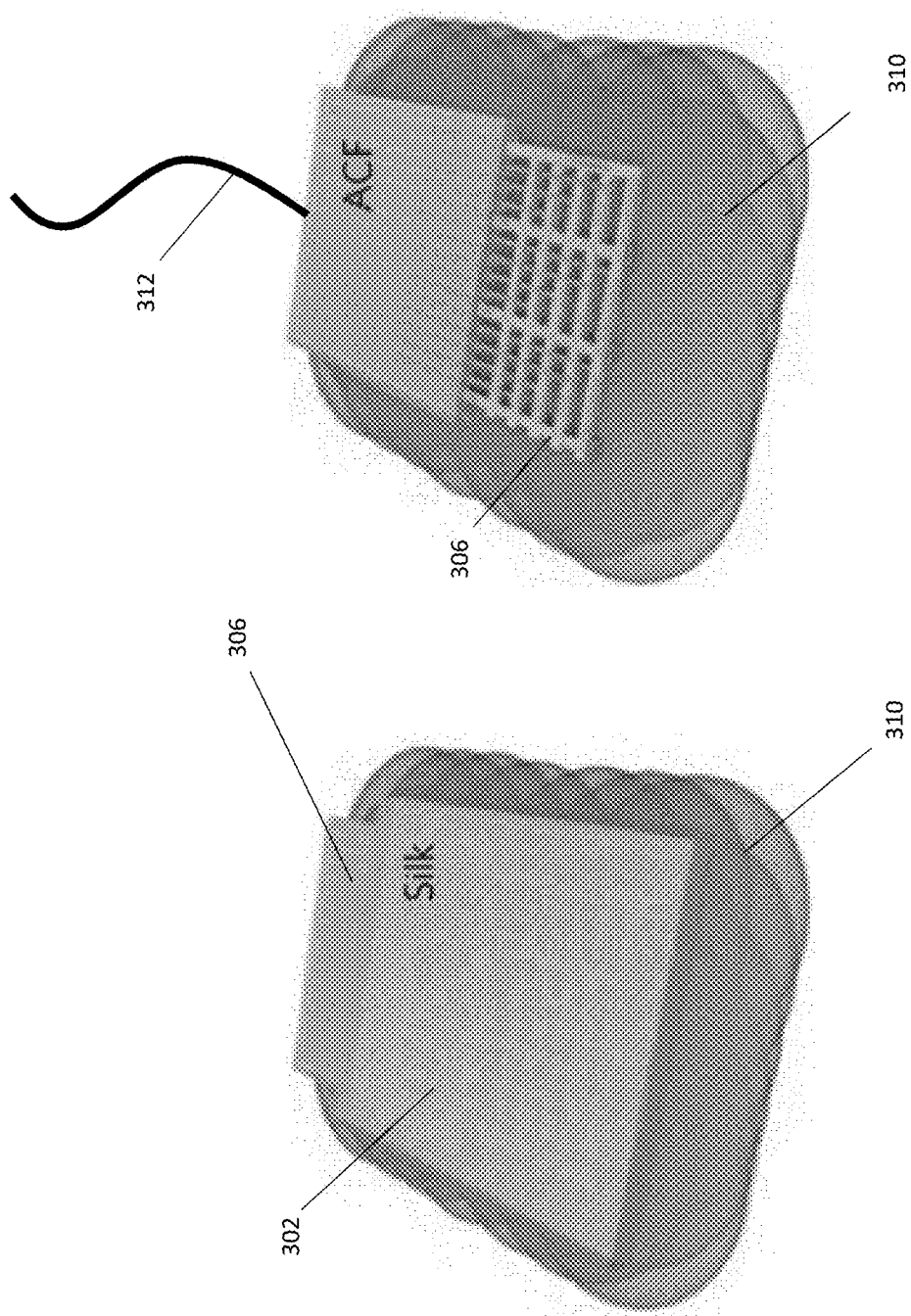

In some embodiments, a high resolution electronic structure is applied to a brain surface. FIGS. 3A-3C illustrate an exemplary process of forming a brain-computer interface. In some embodiments, as is illustrated in FIG. 3A, a high resolution electronic structure 306 on a flexible biocompatible film 302, such as a silk film, can be brought in proximity to an exposed surface of a brain 310. The surface of a brain 310 can be exposed by standard surgical techniques, such as opening a skull with surgical tools.

In some embodiments, after the surface of the brain 310 is exposed, the high resolution electronic structure can be applied to the surface. FIG. 3B is a cross-sectional view illustrating a brain-computer interface after depositing the high resolution electronic structure 306 on a brain surface 310. The biocompatible film 302, such as silk, can sit on top of the high resolution electronic structure 306. The high resolution electronic structure 306 can be directly positioned on the brain surface 310 such that there is direct contact between the components of the electronic structure and neurons on the brain surface 310. The high resolution electronic structure 306 boundaries define an active exposed area of a brain surface. The active exposed area of a brain surface can have an active exposed area, for example, between 1 and 100 cm$^2$.

In some embodiments, the biocompatible film 302 can be removed from the high resolution electronic structure 306 after it is applied to the surface. For example, the biocompatible film 302 can be dissolved. For instance, when the biocompatible film 302 is silk, the biocompatible film can be dissolved with a saline solution. FIG. 3C is a cross-sectional view of the brain-computer interface after dissolution of the flexible film, leaving a high resolution electronic structure 306 on the surface of the brain 310. In some embodiments, as is shown in FIG. 3C, wired contacts 312 can be connected to the high resolution electronic structure to provide power and electronic communication with external devices.

In some embodiments, high resolution electronic structures can include over 1000 electronic components, or over 10,000 components, or over 100,000 components, or even over 1,000,000 electronic components. The high resolution electronic structures can include passive electronic components, active electronic components, or both. In some embodiments, the high resolution electronic structures include a plurality of active electronics.

In some embodiments, brain-computer interfaces include a plurality of components spaced apart such that high resolution sensing can be performed. In some embodiments, some of the plurality of components are spaced apart less than or equal to 10 μm, or less than 5 μm, or less than or equal to 1 μm. In some embodiments, some of the plurality of components are spaced apart such that they can detect and identify a voltage change of a single neuron within a plurality of neurons. In some embodiments, a brain-computer interface can detect a voltage change of each neuron of a plurality of neurons in an active exposed area of a brain surface. In some embodiments, a brain-computer interface can detect a voltage change within a single neuron. In some embodiments, a brain-computer interface can stimulate one or more neurons within a plurality of neurons in an active exposed area of a brain surface. In some embodiments, a brain-computer interface can stimulate each neuron within a plurality of neurons in an active exposed area of a brain surface.

In some embodiments, a brain-computer interface including a high resolution electronic structure is used in medical treatment or diagnostic applications. For example, high resolution electronic structures can be used for treatment and study of epilepsy, such as to map a cortical area of the brain, to reduce or eliminate seizures through neurostimulation, or to pinpoint an epileptic seizure center in a patient.

In some embodiments, high resolution electronic structures can be used for sensory motor applications, such as for prosthetic limb operation. For example, in some embodiments, a high resolution electronic structure can be applied to the brain and can communicate wirelessly or via a wire with a prosthetic device. A patient can be trained to control the prosthetic device through thought, which can include stimulating particular regions of the brain to result in a movement of the prosthetic device.

In some embodiments, high resolution electronic structures can be used for treatment, prevention, or study of neurodegenerative diseases and conditions, such as Parkinson's disease, Turret's syndrome, or epilepsy.

Figure 4:
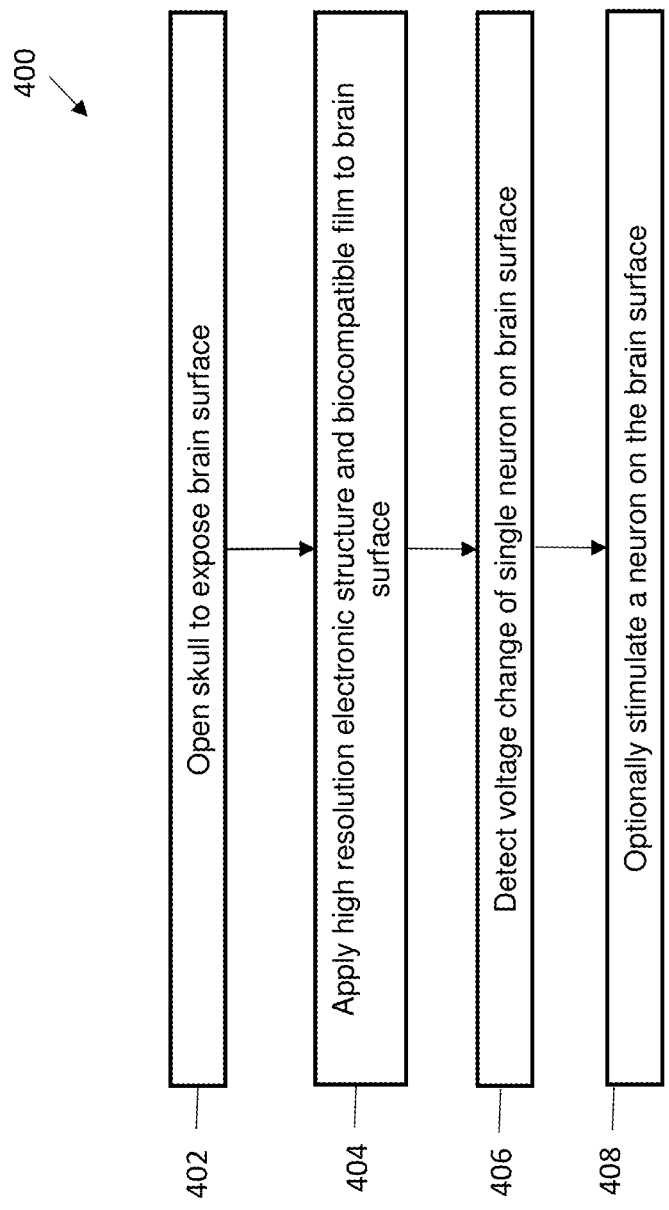
FIG. 4 is a flow diagram illustrating an exemplary method of treating a neurodegenerative disease according to one or more embodiments of the invention.

FIG. 4 is a flow diagram illustrating an exemplary method of treating a neurodegenerative disease 400 according to one or more embodiments of the invention. The method 400 includes opening a skull to expose a brain surface, as is shown at block 402. The method 400 also includes, as shown at block 404, applying a high resolution electronic structure and a biocompatible film to the brain surface. The method 400 also includes, as shown at block 406, detecting a voltage change of a single neuron on the brain surface. The method 400 also includes, as shown at block 408, optionally stimulating a neuron on the brain surface.

In some embodiments, methods include providing an output to an external device. For example, high resolution electronic structures can communicate wirelessly or via a wired communication with any device useful in neurological applications, such as displays, computing devices, prosthetic devices, and the like.

Deposition is any process that grows, coats, or otherwise transfers a material onto a substrate. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography, nanoimprint lithography, and reactive ion etching.

The etching process can include a dry etch (e.g., reactive ion etching, plasma etching, ion beam etching, or laser ablation). The etching process can alternatively include a wet chemical etch (e.g., with potassium hydroxide, or sulfuric acid and hydrogen peroxide). In some exemplary embodiments, both dry etching and wet chemical etching processes can be used. After transferring the pattern, the patterned photoresist is removed utilizing resist stripping processes, for example, ashing. Ashing can be used to remove a photoresist material, amorphous carbon, or organic planarization (OPL) layer. Ashing is performed using a suitable reaction gas, for example, $O_2$, $N_2$, $H_2/N_2$, $O_3$, $CF_4$, or any combination thereof.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of treating a neurodegenerative disease, comprising:
    forming a high resolution electronic structure comprising a plurality of components and a biocompatible film, wherein forming the high resolution electronic structure comprises:
        forming a semiconductor circuit on a silicon substrate, wherein the semiconductor circuit comprises the plurality of components;
        depositing a tensile stress layer on the semiconductor circuit to cause a fracture in the silicon substrate; and
        separating the semiconductor circuit from a portion of the silicon substrate at the fracture in the substrate to generate a semiconductor circuit layer on a thinned silicon layer;
    opening a skull to expose a brain surface;
    applying the high resolution electronic structure to the brain surface; and
    detecting a voltage change of a single neuron on the brain surface with one of the plurality of components.

2. The method according to claim 1, the method further comprising stimulating a neuron with one of the plurality of components.

3. The method according to claim 1, wherein forming the high resolution electronic structure further comprises:
    removing the tensile stress metal layer from the semiconductor circuit; and
    transferring the semiconductor circuit to the biocompatible film.

4. The method according to claim 3, wherein the biocompatible film comprises silk.

5. A method of treating a neurodegenerative disease, comprising:

opening a skull to expose a brain surface;

applying a high resolution electronic structure comprising a plurality of components and a biocompatible film to the brain surface, the biocompatible film comprising a silk film, wherein at least some of the plurality of components are spaced apart at a distance less than or equal to 1 micrometer; and detecting a voltage change of a single neuron on the brain surface with one of the plurality of components.

* * * * *